United States Patent [19]

Currie

[11] 3,955,422
[45] May 11, 1976

[54] SAMPLE SELECTOR APPARATUS AND METHOD

[75] Inventor: Robert D. Currie, Anaconda, Mont.

[73] Assignee: The Anaconda Company, New York, N.Y.

[22] Filed: Nov. 21, 1974

[21] Appl. No.: 525,817

[52] U.S. Cl. .................................... 73/423 R
[51] Int. Cl.² ...................................... G01N 1/20
[58] Field of Search .................. 73/423 R, 422 R

[56] References Cited
UNITED STATES PATENTS

| | | | |
|---|---|---|---|
| 3,511,100 | 5/1970 | Vaughn | 73/423 R |
| 3,575,055 | 4/1971 | Thornton | 73/422 R |
| 3,587,324 | 6/1971 | Bandy | 73/423 R |

*Primary Examiner*—James J. Gill
*Assistant Examiner*—Anthony V. Ciarlante
*Attorney, Agent, or Firm*—Pennie & Edmonds

[57] ABSTRACT

A method and apparatus which are particularly adapted for use in the selective and coordinated abstracting of samples to be examined. Essentially, the selector apparatus which has a support means may embody delivery means, receiving means, collection means, and control means. In a preferred embodiment, the receiving means is operatively connected to the support means and includes a plurality of receptacles for receiving flowable material. The delivery means is supported by the support means and may include at least one, but, desirably a plurality of, movable delivery members which carry flowable material therethrough. Each delivery member is selectively movable between a first position and a second position. Selective operation of the control means is effective to move selected ones of the delivery members to their second positions over the collection means and may return the same to their first positions over the receptacles thereby enabling portions of the flowable material to be separated into the collection means for purposes of subsequently analyzing the same. Also, in the preferred embodiment, a cleaning means may be operated at a preselected time and for a preselected duration between samples being taken for effectively enabling the cleaning of the collection means whenever the delivery members are in their first position.

8 Claims, 3 Drawing Figures

SAMPLE SELECTOR APPARATUS AND METHOD

BACKGROUND OF THE INVENTION

1. Field of the Invention

The present invention is generally directed to a method and apparatus for sorting material and, more particularly, to a method for and sample selecting apparatus which automatically and continuously abstracts preselected ones of multiple samples for subsequent analysis about a single collection means.

2. Description of the Prior Art

It is common practice in the mining industry, for instance, to take samples of suspension of solids in water or the like for purposes of analyzing the constituency thereof. Various heretofore known prior art devices exist for basically providing a proper sample presentation to an on-stream analyzer wherein the samples to be selected and analyzed are periodically withdrawn from slurry streams.

One such known on-stream sampling and analyzing device suffers from several rather significant shortcomings. For example, this particular device employs electro-pneumatically operated sample cutters. Such sample cutters are ordinarily positioned under each of the flowing slurry streams. In practice, the correct positioning of such cutters is a very critical factor in order to have them properly operate, especially from the standpoint of providing a representative sample. Consequently, much time and effort are required to insure this rather precise positioning. Moreover, the electrical contacts normally associated with the cutter shaft present continuous operational problems.

As indicated, such known type of sample selector apparatus employs electro-pneumatic mechanisms. These mechanisms normally utilize the surrounding ambient air for the successful operation thereof. It may happen, however, that the ambient air surrounding such sample selector apparatus is subject to freezing and extreme weather conditions, and as a result thereof, the pneumatic mechanisms tend to lose some air. In effect, the cold air adversely affects the pneumatic mechanisms to the extent that they tend to step out of phase with a computer operatively associated therewith for controlling the same. Consequently, loss of assay ability during this period results. Obviously, such condition contributes to inaccuracies in sample read-outs.

In addition to the foregoing mentioned shortcomings prevalent with the above-noted type of sample selector apparatus, there is an added shortcoming in that such sample selector is totally enclosed. By virtue of this enclosure, detection of mechanism problems with the equipment and components are substantially prevented. Since the sample selector apparatus is totally enclosed, it is also virtually difficult to detect any sample problems, such as with flow volume or sample contamination. Furthermore, this particular selector apparatus is rather complicated in construction and, as a result thereof, repairs are somewhat costly and rather frequently required. Accordingly, it will be appreciated that with a greater frequency of repair there is a corresponding increase in apparatus downtime. Hence, a less efficient and economic operation results.

Difficulties are also encountered by reason of the fact that, if failure of one of the slurry units occurs, such failure adversely affects sample positions at other slurry units. Another debilitating factor which is associated with such aforenoted types of sampling apparatus is the contamination which may result whenever multiple samples are taken and presented to an on-stream analyzer. Consequently, of course, the sample readouts provided are not as accurate as otherwise would be desired and required.

SUMMARY OF THE INVENTION

Briefly stated, the present invention is directed to an improved process and apparatus particularly adapted for overcoming the disadvantages described in the prior art, and for selectively abstracting either simultaneously or successively respective ones of a plurality of samples to be examined in an automatic, compact, and coordinated manner which tends to minimize sample contamination.

In furtherance of the present invention, it is contemplated that the selector apparatus essentially embody delivery means, receiving means, collection means, and control means. In a preferred embodiment, the receiving means includes a plurality of receptacles so arranged that the collection means is centrally located with respect to such receptacles. The delivery means is appropriately supported by a support structure of the sample selector apparatus and may include at least one, but desirably a plurality, of swingable pipes which carry flowable material therethrough. Each swingable pipe is normally positioned so that its discharge end is situated above at least one receptacle for normally delivering the material thereinto. Selective operation of the control means is effective to deflect or swing the discharge end of the swingable pipe over the collection means and may, after a period of time, return the same to its original position to thereby enable a portion of the flowable material to be separated into the collection means for purposes of analyzing the same. Also, in the preferred embodiment, a cleaning means may be operated at completion of the last-noted operation for effectively and in a controlled sequence cleaning the collection means so as to thereby tend to reduce the likelihood of contamination of other samples which are desired to be taken.

By virtue of the above-preferred constructional arrangement of a sample selector apparatus of the present invention, there is enabled to be performed a process adapted for use in abstracting samples of flowable material which comprises the steps of: arranging a plurality of delivery members which carry flowable material laterally with respect to a centrally located collection means, moving selected tubes such that discharge ends thereof are positioned over the centrally located collection means for discharging flowable material thereinto, returning the selected delivery members to a position such that the discharge ends are no longer positioned over the collection means and selectively distributing fluid to the collection means for cleaning the surfaces of such collection means thereby tending to diminish or eliminate undesired materials from the collection means prior to said step of selectively discharging the flowable material into the collection means.

BRIEF DESCRIPTION OF THE DRAWINGS

The above as well as other objects, features, and advantages of the present invention will become apparent upon a reading of a detailed description thereof when viewed in conjunction with the accompanying drawings wherein like structures throughout the several views are indicated by like reference numerals.

DESCRIPTION OF A PREFERRED EMBODIMENT

Figure 1:
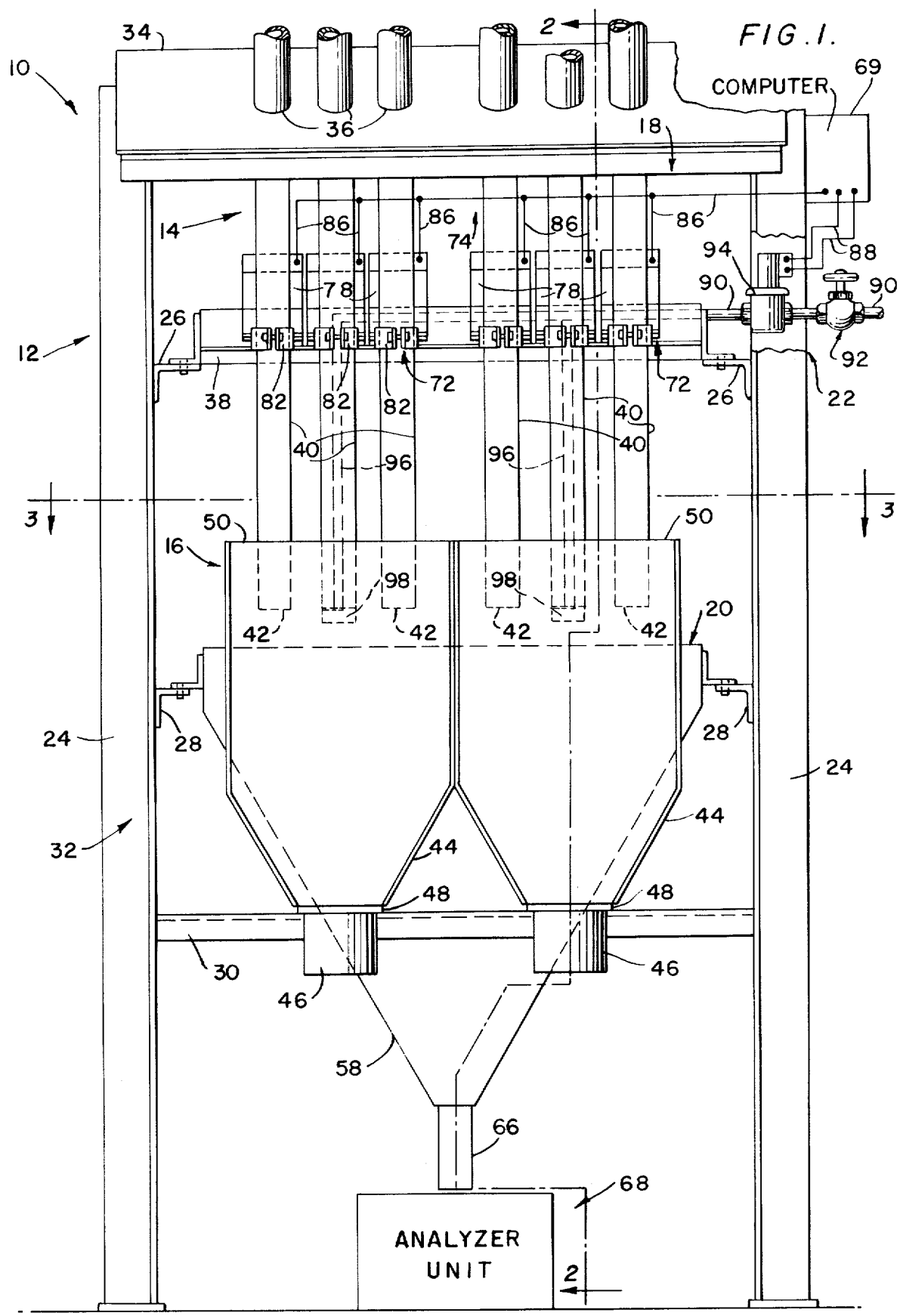
FIG. 1 is a side elevational view of a sample selector apparatus embodying the principles of the present invention.
Figure 2:
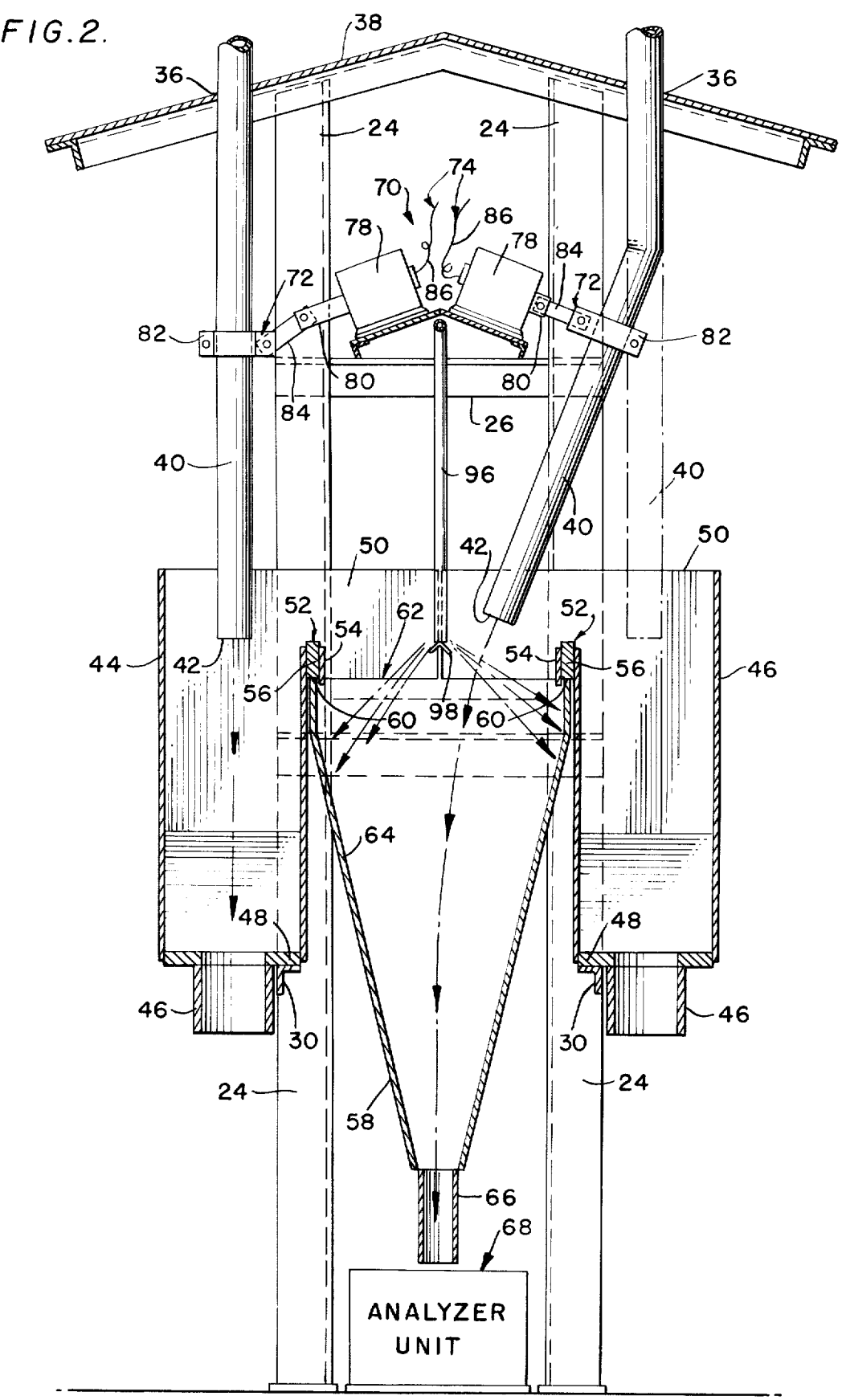
FIG. 2 is a sectional view taken substantially along section line 2—2 in FIG. 1 looking in the direction of the arrows illustrating additional features of the present invention.
Figure 3:
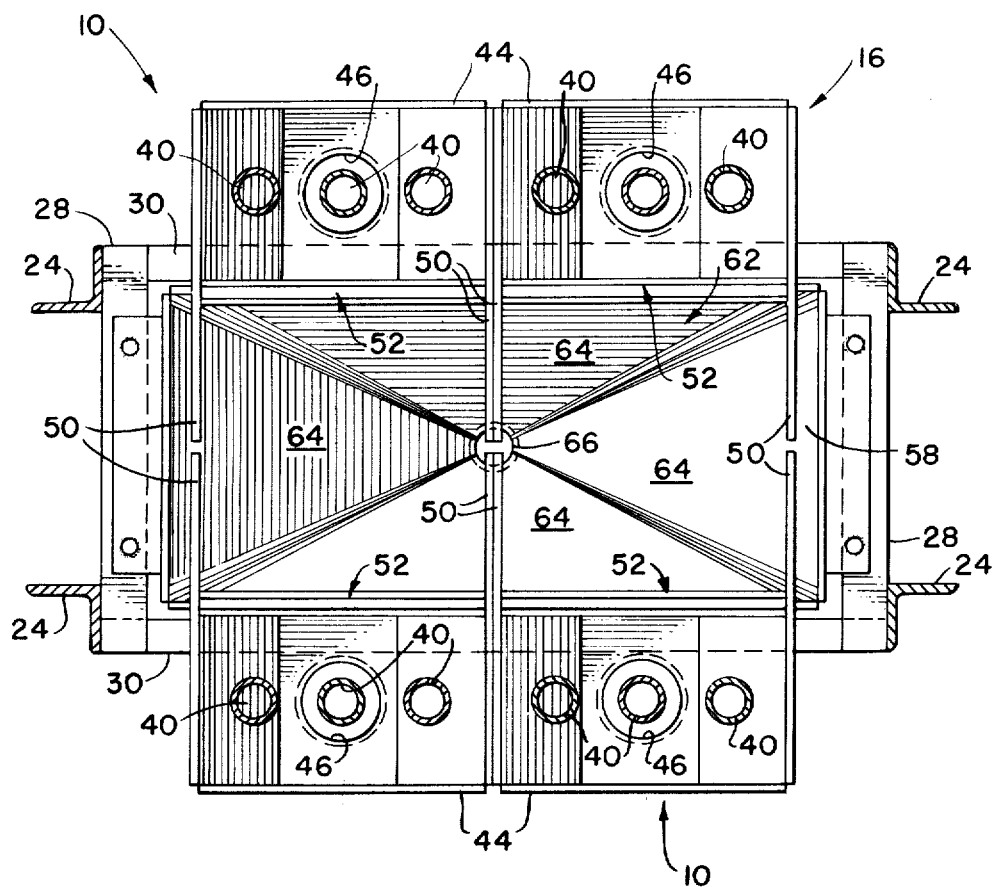
FIG. 3 is a sectional view taken substantially along section line 3—3 in FIG. 1 looking in the direction of the arrows and illustrating still further features of the present invention.

With respect to FIGS. 1 to 3 of the drawings, there is clearly depicted an automatic sample selector apparatus embodying the principles of the present invention and generally designated by reference numeral 10. Notwithstanding that the subsequent description is connected with a sample selector apparatus which is particularly useful in the coordinated and uninterrupted sequence of operations used to obtain selected slurry samples in ore plants for purposes of assaying the same, it should be herein emphasized that the theory and practice of the instant invention enable it to be used in other situations, wherein it is desired to continuously and automatically sample selected ones of multiple flowable streams of material at a central location.

In the illustrated embodiment, the sample selector apparatus 10 which is contemplated by the present invention essentially includes support means 12, delivery means 14, material receiving means 16, control means 18, collection means 20, and cleaning means 22.

The support means 12 includes four upright structural support members 24 which are made of a suitable structural material. Pairs of upper, intermediate, and lower generally elongated horizontal structural support members 26, 28, and 30, respectively, are suitably connected, as by welding or riveting, between the upright support members 24 as indicated in FIGS. 1 to 3, and are appropriately vertically spaced with respect to each other. Such constructional arrangement provides for a relatively rigid support frame 32 for the automatic sample selector apparatus 10. The support frame 32 may be fabricated from any suitable structural material which should possess rigidity and be able to adequately withstand outdoor usage. Attached, in a conventional fashion, to the topmost portions of the upright support members 24 is a generally pitched upper covering member 34, the purpose of which is to serve to prevent dirt and other debris from entering into the collection means 20. Opposed longitudinal sides of the covering member 34 are provided with mounting apertures 36 which cooperate the delivery means 14 in a manner to be presently described. Fixedly secured to and supported by the upper generally horizontal structural support members 26 is a sloped support platform 38 for supporting a portion of the control means 18. The intermediate and lower horizontal support members 28 and 30, respectively, are adapted to support the collection means 20 and the receiving means 16 of the present invention in any conventional fashion.

With particular reference to FIGS. 1 and 2, the delivery apparatus or means 14 of the present invention may comprise a plurality of separate and spaced apart sample delivery tube or pipe members 40 which are selectively swingable or pivoted from a first or normally vertical position to a second or inclined position, such as clearly illustrated in FIG. 2. Each of the tubes 40 are respectively fitted through the apertures 36. In the vertical position, discharge end 42 of each of these delivery tube members 40 is located above the receiving means 16 for discharging the flowable material carried by the tube member 40 thereinto, whereas, when, in the inclined position, the tube members 40 are arranged over the collection means 20. Accordingly, the flowable material which is carried by the tube members 40 is discharged into the collection means 20. It is envisioned that the sample delivery tubes 40 of the present invention may be made in any conventional fashion and from conventional material. Although the tubes 40 are shown as being made of a generally flexible material, nevertheless, other suitable and well-known types of sample delivery tube members may be utilized so long as they are swingable between the aforenoted vertical and inclined positions. Hence, a known type of pivoting arrangement might be provided. Such sample delivery tubes 40 are particularly adapted to continuously deliver streams of ore pulp or slurry from various collection points in a concentrator plant into the sample receiving means 16. After passage through the sample receiving means 16, in a manner to be described, the flowing streams of ore pulp are returned to an appropriate point in the concentrator plant circuit.

With continued reference to FIGS. 1 to 3, the sample receiving means 16 is basically comprised of a plurality of receptacles or rejection hoppers 44. The rejection hoppers 44 are arranged so as to cluster about a single and centrally located collection means 20. The particular significance of such arrangement is that it enables a realtively compact apparatus to be assembled. In the illustrated embodiment, each of the hoppers 44 has an outlet orifice 46 which is appropriately connected to a conventional conduit (not shown), and a support portion 48 thereof supported by the lower horizontal support members 30, as perhaps best indicated in FIG. 2. In addition, as is denoted in the drawings, sets of three delivery tube members 40 protrude into each rejection hopper 44. Integrally located at the top of the rejection hoppers are partition walls 50 and a mounting device generally indicated by reference numeral 52. The partition walls 50 are arranged to project across the collection means 20 and also tend to stabilize such hoppers 44 thereon. Each of the mounting devices 52 includes an overhanging portion 54 and a mounting block 56. The mounting block 56 is designed to rest upon collection means 20 while the overhanging portion 54 overlaps the collection means to aid in supporting such hoppers 44. In such a manner, the rejection hoppers 44 are adequately and removably supported by collection means 20.

In the illustrated embodiment, the collection means 20 is defined by a single sample collection hopper 58 which may be of any suitable construction. The collection hopper 58 has opposed longitudinally extending edges 60 which cooperate with the mounting device 52 such that mounting blocks 56 rest thereon while overhanging portions 54 extend into an inlet opening 62 for hopper 58. Side walls 64 of the collection hopper 58 converge to a sample outlet orifice 66. Such sample outlet 66 is shown as situated vertically above any well-known and suitable type of on-stream analyzer unit 68. Since such an analyzer unit 68 is conventional, details as to its construction and operation are not believed essential to an adequate understanding of the present invention. An example of an on-stream analyzer unit 68 which may be successfully used to assay the slurry discharge from respective ones of the delivery tubes 40 may include appropriate suitable X-ray units. It should, of course, be mentioned that the sample outlet orifice 66 is connected to the analyzer unit 68 in a contemporary fashion. Hence, details as to this connection have been omitted.

As perhaps more particularly pointed out in FIG. 3 and as previously discussed, the sample rejection hoppers 44 are laterally and, preferably, symmetrically situated with respect to the centrally located sample collection hopper 58. By virtue of this clustered arrangement, the delivery tubes 40 whenever selectively actuated so as to be deflected to their inclined positions, the respective samples of flowing slurry may be centrally and compactly handled through a single collection hopper 58 as opposed to having individual onstream analyzers associated with respective ones of the sample delivery tubes 40. Accordingly, a simple, efficient, and compact sample selecting structure is furnished which enhances the selective assaying of materials flowing through delivery tubes 40.

The control mechanism or means 18 enables the selected, coordinated, and uninterrupted sequence of operations of the delivery means 14 and cleaning means 22 in a manner to be more fully described. Essentially, such control means 18 is elecrically operatively connected to a suitable type computer 69 or other like device which provides for the noted sequence of operations. Control means 18 basically includes deflection means 70, motion transmitting means 72, and first and second enabling means 74 and 76, respectively.

As clearly depicted in FIGS. 1 and 2, the deflection means 70 may include a plurality of suitable solenoid devices 78. In this particular embodiment, two opposed banks of solenoids 78 are provided. Each bank is comprised of six solenoid devices 78 with each one of the solenoids being operatively connected to a respective delivery tube 40. The solenoid devices 78 may be of any well-known construction and are assembled in a known manner. Each solenoid device 78 includes a protruding deflection plunger 80 which is selectively reciprocated in either direction along its longitudinal axis depending upon appropriate energization of the solenoid 78. Moreover, respective ones of the solenoids 78 are, in a conventional fashion, operatively mechanically secured to the support platform 38, which is, in turn, supported by and secured to the upper horizontal support members 26. The plungers 80 are connected to motion transmitting means 72 which themselves are, in turn, detachably secured to the delivery tubes 40. It should be noted, from the embodiment illustrated, that each of the individual solenoid devices 78 is associated with respective ones of the motion transmitting means 72. Each motion transmitting means 72 of the instant embodiment basically includes a locking clamp 82 and a motion transmitting link 84. The locking clamp 82 is appropriately secured to a delivery tube 40 below a desired pivot or flexure point therefor. Pivotally interconnected between the deflection plunger 80 and clamp 82 is the motion transmitting link 84 which serves to swing the clamp 82 and thereby the delivery tube 40 in response to selective energization of the solenoid device 78. By virtue of this constructional arrangement, whenever the deflection plungers 80 are retracted, they will through transmitting links 84 and clamps 82 pivot or deflect the delivery tube 40 inwardly towards and over the inlet opening 62 of the collection hopper 58 or to their second position. And whenever the plungers 80 are extended they serve to return the delivery tubes 40 back to their first position whereat the material flowing therethrough is discharged into the appropriate rejection hoppers 44.

First enabling means 74 is depicted as including at least a terminal lead 86 which is appropriately electrically connected to the solenoid devices 78 and to the computer 69 for purposes of enabling selective energizing or deenergizing the solenoid devices 78 in accordance with a suitable program for the computer. The second enabling means 76 is depicted as a pair of terminals 88 which are operatively electrically interconnected between the cleaning means 22 and the computer 69 for reasons which will afterwards be more fully described. It shall be understood, of course, that the present invention contemplates that any appropriate well-known type of electrical wiring arrangement extend between the computer 69 and solenoid devices 78 as well as the cleaning means 22.

In connection with the cleaning system or means 22 of the present invention, reference is made to FIGS. 1 and 2. Basically, the cleaning means 22 includes fluid supply lines 90, manual control valve 92, solenoid operated valve 94, dispensing tubes 96, and deflectors 98. The supply lines 90 are connected to a source (not shown) of appropriate cleaning fluid, such as, for example, water. The manually controlled valve 92 and solenoid operated valve 94 may be of any well-known type in the art and are suitably connected with the supply tube 90 for regulating the flow of water to the collection hopper 58 for purposes afterwards made apparent. The manually controlled valves allows for independent cleaning of the collection means 20. The solenoid valve 94 is electrically operatively connected to the second enabling means 76 which, in turn, is operatively connected to the computer 69. The second enabling means 76 enables the selective energization-deenergization of the solenoid 78. Thus, in the preferred embodiment, the computer 69 is arranged, in response to an appropriate program, to selectively energize the solenoid valve 94 so as to allow the fluid from the source to flow therethrough and eventually to and through the collection hopper 58. It is contemplated by the present invention that energization of the solenoid valve 94 be timed in sequence with the operation of the delivery tubes 40 such that after every sample is taken from the tubes 40 the solenoid valve is opened to the extent that it permits the cleaning fluid to flow toward the collection hopper 58. It should, of course, be pointed out that with deenergization of the solenoid valve 94 such valve is caused to close thereby precluding flow to the collection hopper 58. However, once the fluid flows past the valve 94 it enters and descends through the dispensing tubes 96. The deflectors 98 are connected to and terminate at the end of the dispensing tubes 96. These deflectors 98 may have a generally V-shape and serve to divide to the flowing fluid into two streams which are generally directed in opposite directions with respect to each other.

It is, of course, apparent that such streams of fluid will clean from the side walls 64 of the collection hopper 58 accumulated debris or the like which had been deposited from previous samples. Also, the time duration of the fluid dispensing operation is preselected through the computer 69. Although the computer 69 has been described for use in conjunction with the deflection means 70 as well as with the cleaning means 22, it should again be emphasized that the solenoid devices 78 and solenoid valve 94 of the instant invention may be successfully operated in a coordinated and preselected manner by any other suitable and well-known means without departing from the spirit and scope of the present invention. Additionally, the manual control valve 92 may be independently operated to provide for cleaning of the collection means 20.

By reason of the foregoing description of a preferred embodiment, its mode of operation is believed readily apparent. However, to facilitate a better understanding of the new and improved method and apparatus, it will be appreciated that, whenever it is desired to assay or analyze the slurry flowing through one or more of the delivery tubes 40, a particular solenoid device 78 which is operatively associated therewith is energized as a result of activation by the computer. During the energization of the solenoid device 78, its plunger 80 is correspondingly retracted. Accordingly, motion transmitting link 84 and clamp 82 will conjointly move therewith, and, in so doing, pivot or bend the particular delivery tube 40. As a consequence of this movement, the discharge end 42 of the delivery tube 40 will move from its vertical position, over one of the rejection hoppers 44, to an inclined position, whereat such discharge end 82 is located over the collection hopper 58 for discharging therein a sample of the slurry material.

This sample of slurry will, accordingly, pass through the sample orifice 66 and into the analyzer unit 68 for purposes of analyzing the contents thereof. Since solenoids 78 are used as opposed to electro-pneumatic actuators, they will, of course, not be subject to the aforenoted disadvantages associated with cold temperatures affecting the air employed in such actuators. After a controlled amount of slurry has been obtained, the solenoid 78 is appropriately deenergized. Such deenergization results in the plunger 80 moving outwardly and the delivery tube 40 being swung back to its original vertical position. Whenever in this latter position, the slurry will resume its travel through the rejection hoppers to other portions of the ore plant. The time interval in which the discharge outlet 48 is located over the collection hopper 58 so as to dispense the material therein is preselected by the computer 69.

Upon resumption of the delivery tubes 40 to their vertical positions, the solenoid valve 94 is energized so as to allow flow of the cleaning fluid through the supply line 90, dispensing tubes 96 and around the deflectors 98 into collection hopper 58. Hence, the fluid will serve to clean the collection hopper 58 and flush the debris through the outlet orifice 66. Similarly, the operation of the cleaning means 22 may be timed to commence at the end of each sample abstracting operation and terminate prior to another sample abstracting process. Thusly, the cleaning operation is performed in a selective and coordinated manner. In this fashion, the likelihood of sample contamination is significantly reduced or may even be eliminated. While only the action of one delivery tube 40 has been aforedescribed, as aforementioned, selected ones of the delivery tubes 40 may be selectively actuated either successively or simultaneously so as to abstract samples of material therefrom at a central collection means. By reason of the clustered arrangement or rejection hoppers 44 generally centered about the collection hopper 58, multiple samples from several delivery tubes may be abstracted and forwarded to a single on-stream analyzer unit.

By reason of applicant's novel and improved method and apparatus, abstracting of samples of material may be carried out in a compact, coordinated, and preselected fashion. Such samples may be attained without loss of assay ability as a result of the adverse effects of cold weather. Moreover, by virtue of its relatively open or non-enclosed and simple construction, it enables personnel to detect sample problems, such as flow volume or sample contamination, as well as reduce the likelihood and cost of repairs. Furthermore, the integral combination with a cleaning means which is operated in a coordinated and preselected fashion serves to clean a central collection means between samples so as to thereby minimize sample contamination.

While the invention has been described in connection with the foregoing embodiments, it is not intended to limit the invention to the particular form set forth above, but, on the contrary, it is intended to cover such alternatives, modifications, and equivalents as may be included within the spirit and scope of the invention as defined by the appended claims.

What is claimed is:

1. An automatic sample selector apparatus having a support means and being adapted to use in selectively abstracting samples to be examined comprising delivery means supported by the support means including a plurality of movable delivery members for discharging flowable material, receiving means operatively connected to the support means for receiving and directing the flowable material, collection means connected to the support means for selectively receiving flowable material, said receiving means including a plurality of stationary receptacles spaced adjacent each other and said collection means being generally centrally located with respect to said receptacles such that said receptacles generally surround said collection means, control means being operatively connected to said delivery means for selectively moving the delivery member towards and away from said collection means and said receptacles so as to selectively enable the delivery member to discharge the flowable material into said collection means for enabling the discharged material to be subsequently examined, and means operatively connected to said control means and being energizable by said control means to discharge a cleaning fluid to said collection means for cleaning said collection means of accumulated impurities.

2. An apparatus as set forth in claim 1 in which said control means includes deflection means associated with each of said delivery members, and motion transmitting means connected to said deflection means, respective ones of said delivery members being operatively connected to a respective one of said motion transmitting means for conjoint movement therewith, at least one of said deflection means being selectively energized to move said motion transmitting means to thereby move said delivery member from a first position, whereat said delivery member is located over its respective said receptacle, to a second position, whereat said delivery member is moved so as to be situated over said collection means.

3. An apparatus as set forth in claim 2 in which said deflection means includes energizable solenoid devices having a plunger connected therewith for reciprocal movement therewith.

4. An apparatus as set forth in claim 1 in which said means for discharging cleaning fluid includes at least one valve means being actuated by said control means for enabling the fluid to flow to said collection means for a time interval after and before said delivery means discharges a sample from at least said delivery member into said collection means.

5. In an automatic sample selector apparatus having a support means and being adapted for use in selectively abstracting samples to be examined comprising delivery means supported by the support means and having a plurality of movable delivery members for discharging flowable material therethrough and each being individually operated for movement from a first position to a second position; receiving means operatively connected to the support means and including a plurality of stationary receptacles for receiving the flowable material whenever respective ones of said delivery members are in said first position; collection means generally centrally located with respect to each of said plurality of receptacles for receiving the flowable material whenever respective ones of said delivery members are located at said second position for abstracting a portion of the flowable material; cleaning means operatively connected to the support means for dispensing cleaning fluid to said collection means; and control means operatively connected to said delivery means and said cleaning means for moving selected ones of said delivery members from said first position to said second position over said collection means in a coordinated and preselected manner, and for selectively operating said cleaning means at a preselected time and for a preselected duration for enabling dispensing of cleaning fluid to said collection means to thereby clean said collection means whenever said delivery members are in said first position.

6. In an automatic sample selector apparatus having a support means and being adapted for use in selectively abstracting samples to be examined comprising delivery means supported by the support means and having a plurality of delivery members, each of which discharge flowable material therethrough and being operated for movement from a first position to a second position; receiving means operatively connected to the support means and including a plurality of stationary receptacles for receiving the flowable material whenever respective ones of said delivery members are in said first position; collection means operatively associated with said receiving means generally centrally located with respect to said plurality of said receptacles for receiving the flowable material whenever respective ones of said delivery members are located at said second position for abstracting a portion of the flowable material; cleaning means operatively connected to said collection means and including at least a solenoid operated valve and a discharge tube connected thereto; and control means operatively connected to said cleaning means and said delivery means including deflection means, motion transmitting means, and first and second enabling means, said deflection means including a plurality of solenoids, said motion transmitting means interconnecting respective ones of said delivery members to respective ones of solenoids for transmitting motion to respective ones of delivery members for moving said delivery members from said first position to said second position in response to actuation of said solenoid, said first enabling means being connected to respective ones of said solenoids for enabling selective actuation of said solenoids in a coordinated and preselected manner such that preselected ones of said delivery members are movable between said first and second positions, said second enabling means connected to said solenoid valve for enabling selective operation of said valve at a preselected time and for a preselected duration for enabling dispensing of cleaning fluid to said collection means to thereby clean said collection means whenever said delivery members are in said first positions.

7. A process adapted for use in the abstracting of samples of flowable material comprising the steps of: arranging a plurality of discharge tubes which carry flowable material and a plurality of stationary receptacles laterally with respect to a centrally located collection device, moving selected tubes from a position over the receptacles to a position such that discharge ends thereof are positioned over the centrally located collection device for discharging flowable material thereinto, returning the selected tubes to a position such that the discharge ends are no longer positioned over the collection device but over at least one receptacle.

8. A process adapted for use in abstracting samples of flowable material comprising the steps of: arranging a plurality of discharge tubes which carry flowable material and a plurality of stationary receptacles laterally with respect to a centrally located collection device, moving selected tubes from a position over the receptacles to a position such that discharge ends thereof are positioned over the centrally located collection device for discharging flowable material thereinto, returning the selected tubes to a position such that the discharge ends are no longer positioned over the collection device but over at least one receptacle, and selectively distributing fluid to the collection device for cleaning such collection device thereby tending to diminish or eliminate undesired materials from the collection device prior to said step of selectively discharging the flowable material into the collection device.

* * * * *